United States Patent [19]

Herber et al.

[11] Patent Number: 4,806,624

[45] Date of Patent: Feb. 21, 1989

[54] DEHYDROGENATION OF DEHYDROGENATABLE HYDROCARBONS

[75] Inventors: Raymond R. Herber, Medinah; Gregory J. Thompson, Park Ridge, both of Ill.

[73] Assignee: UOP Inc., Des Plaines, Ill.

[21] Appl. No.: 63,058

[22] Filed: Jun. 17, 1987

[51] Int. Cl.[4] .......................... C07C 4/02; C07C 2/64; C07C 5/327

[52] U.S. Cl. .................................. 585/440; 585/444; 585/445; 585/654; 585/660; 585/662

[58] Field of Search ............... 585/444, 445, 660, 662, 585/440, 654

[56] References Cited

U.S. PATENT DOCUMENTS

| | | | |
|---|---|---|---|
| 2,959,626 | 11/1960 | Krausse et al. | 260/674 |
| 3,391,218 | 7/1968 | Bloch | 260/683.3 |
| 3,409,689 | 11/1968 | Ward | 260/669 |
| 3,437,703 | 4/1969 | Reitmeier et al. | 260/669 |
| 3,448,165 | 6/1969 | Bloch | 260/683.3 |
| 3,502,737 | 3/1970 | Ghublikian | 260/669 |
| 3,515,766 | 6/1970 | Root et al. | 260/669 |
| 3,647,911 | 3/1972 | Vesely et al. | 260/683.3 |
| 3,649,566 | 3/1972 | Hayes et al. | 252/470 |
| 3,714,281 | 1/1973 | Hayes et al. | 260/668 D |
| 3,761,390 | 9/1973 | Greenwood et al. | 208/65 |
| 3,855,330 | 12/1974 | Mendelsohn et al. | 260/669 |
| 3,907,511 | 9/1975 | Forbes et al. | 23/288 G |
| 4,418,237 | 11/1983 | Imai | 585/443 |
| 4,435,607 | 3/1984 | Imai | 585/443 |

Primary Examiner—Curtis R. Davis
Attorney, Agent, or Firm—Thomas K. McBride; John G. Tolomei; John G. Cutts, Jr.

[57] ABSTRACT

A process for the catalytic dehydrogenation of a dehydrogenatable $C_2$-plus feed hydrocarbon which comprises the steps of: (a) passing a feed stream comprising the $C_2$-plus feed hydrocarbon into a dehydrogenation zone and through at least one bed of dehydrogenation catalyst maintained at dehydrogenation conditions and producing a dehydrogenation zone effluent stream comprising hydrogen, the $C_2$-plus feed hydrocarbon and a $C_2$-plus product hydrocarbon; (b) forming an oxidation catalyst bed feed stream by admixing an oxygen-containing stream with the dehydrogenation zone effluent stream; (c) passing the oxidation catalyst bed feed stream through a bed of hydrogen selective oxidation catalyst maintained at selective oxidation conditions and producing an oxidation zone effluent stream having a reduced concentration of hydrogen; and (d) recovering the product hydrocarbon from the oxidation zone effluent stream without contacting the oxidation zone effluent stream with dehydrogenation catalyst.

24 Claims, 1 Drawing Sheet

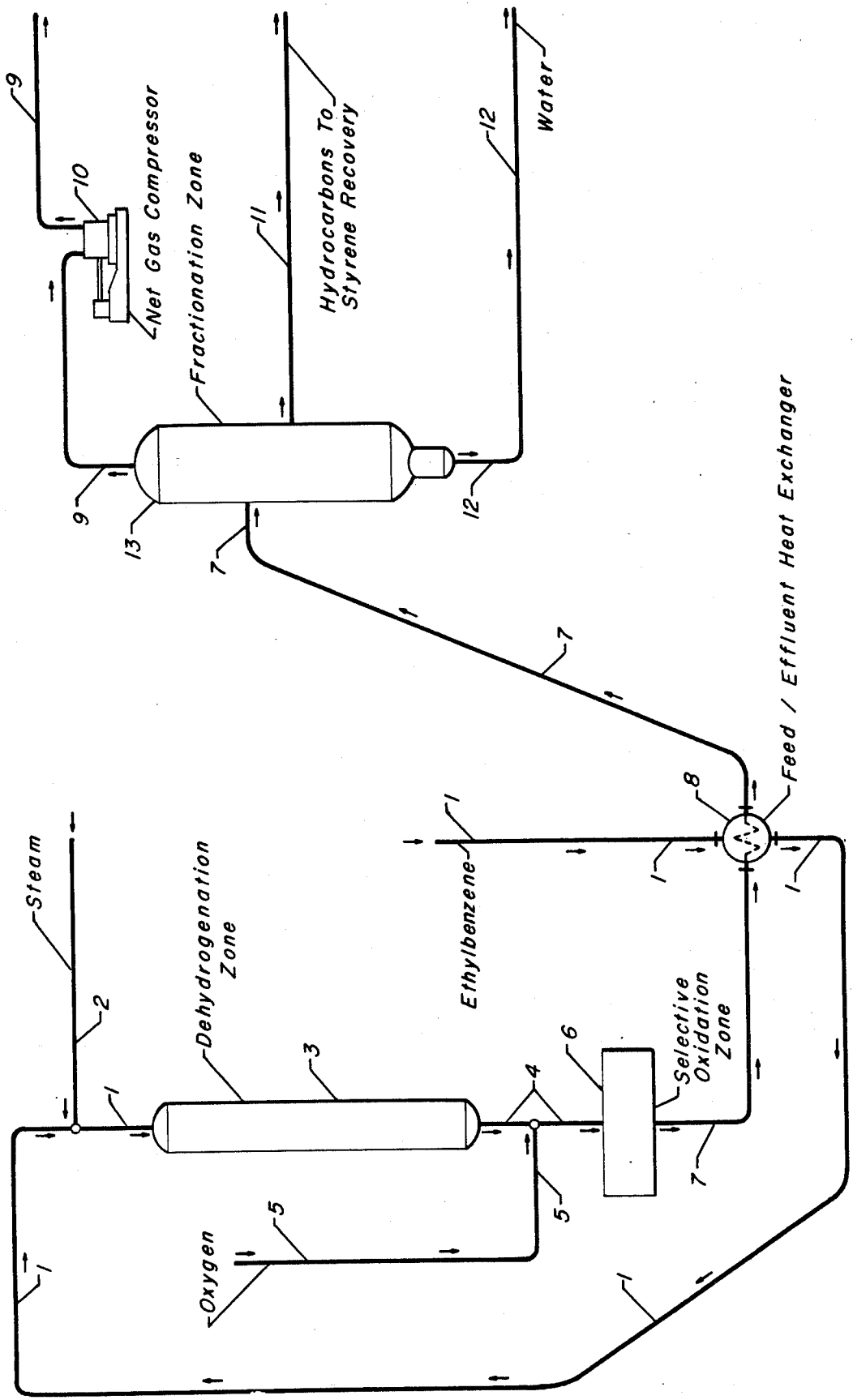

DEHYDROGENATION OF DEHYDROGENATABLE HYDROCARBONS

BACKGROUND OF THE INVENTION

The field of art to which this invention pertains is the catalytic dehydrogenation of a dehydrogenatable hydrocarbon to produce an olefinic or aromatic hydrocarbon. The preferred use of the subject method is in the dehydrogenation of alkylaromatic hydrocarbons such as the conversion of ethylbenzene to styrene. The invention is specifically related to the injection of an oxygen-containing gas into a bed of selective hydrogen oxidation catalyst located in the dehydrogenation zone effluent stream.

INFORMATION DISCLOSURE

The dehydrogenation of hydrocarbons is well described in the prior art, with both acyclic and aromatic hydrocarbons being thereby converted to the corresponding less saturated products. For instance, dehydrogenation is performed commercially for the production of styrene from ethylbenzene to fulfill the sizable demand for this polymer precursor. U.S. Pat. No. 3,515,766 (Root et al) and U.S. Pat. No. 3,409,689 (Ward) show typical prior art catalytic steam dehydrogenation processes for alkylaromatics including ethylbenzene. These references describe the admixture of superheated steam into the feed hydrocarbon and the admixture of additional amounts of superheated steam with the reactants between sequential beds of dehydrogenation catalyst to reheat the reactants.

The dehydrogenation of low molecular weight paraffin hydrocarbons is a highly developed process. For instance, processes for the dehydrogenation of paraffins are described in U.S. Pat. Nos. 3,391,218; 3,448,165; 3,649,566; 3,647,911; and 3,714,281. These references describe various catalysts and process conditions which may be employed.

A typical prior art process flow comprises the admixture of the feed hydrocarbon with hydrogen and the heating of the feed stream through indirect heat exchange with the dehydrogenation zone effluent stream. The feed stream may comprise recycled unconverted hydrocarbons and will normally comprise recycled hydrogen. After being heated in the feed-effluent heat exchanger, the feed stream is further heated by passage through a heater which is typically a fired heater or furnace. The feed stream is then contacted with a bed of dehydrogenation catalyst, which may be either a fixed, moving or fluidized bed of catalyst. The dehydrogenation reaction is very endothermic and the entering reactants are quickly cooled to temperatures at which the dehydrogenation reaction does not proceed at an acceptable rate. To counteract this cooling effect of the reaction, heat may be supplied to the bed of dehydrogenation catalyst by indirect heat exchange with circulating high temperature fluids or by a rapid turnover of catalyst in a fluidized bed system.

Another method of supplying the necessary heat of reaction is to remove the reactants from the bed of dehydrogenation catalyst and to heat the reactants externally through the use of a heater. In this instance the reactants which emerge from the first bed of dehydrogenation catalyst are passed through a heater which may be similar to the initial feed heater. The thus-heated reactants are then passed through a second bed of dehydrogenation catalyst. This contacting-reheating sequence may be repeated as many times as desired. A process for the dehydrogenation of ethylbenzene utilizing interstage reheating of the reactants is described in U.S. Pat. No. 2,959,626.

Still another method of reheating the reactants in a multistage dehydrogenation process is through the use of superheated steam, which can be admixed into the feed stream to the first reaction stage and/or to each subsequent reaction stage. This type of interstage reheating is normally associated with the dehydrogenation of alkylaromatic hydrocarbons and is described in U.S. Pat. No. 3,515,766.

Whatever form the reaction zone takes, it is customary for the effluent stream of the dehydrogenation reaction zone to be passed through the feed-effluent heat exchanger for heat recovery and to then be cooled sufficiently to cause a partial condensation of the effluent stream. The partial condensation facilitates the easy separation of the bulk of the hydrogen from the other components of the effluent stream, with a portion of the hydrogen being removed as a net product gas and a second portion normally being recycled to the dehydrogenation reaction zone. The remaining mixture of saturated and unsaturated hydrocarbons and by-products is bypassed into the appropriate products recovery facilities, which will typically comprise a first stripping column which removes light ends having boiling points below that of the desired product and a second fractionation column which separates the remaining hydrocarbons into product and recycle streams.

It is also known in the prior art to pass oxygen into a dehydrogenation zone for the purpose of reacting the oxygen with hydrogen released during the dehydrogenation reaction to thereby liberate heat and to consume hydrogen. The processes known to employ this technique utilize a hydrogen oxidation catalyst in an attempt to selectively oxidize the hydrogen rather than feed or product hydrocarbons also present in the dehydrogenation zone. For instance, U.S. Pat. No. 3,437,703 (Reitmeir et al) discloses a dehydrogenation process which may utilize either a "homogeneous catalyst system" in which oxidation and dehydrogenation catalysts are admixed or a layered system of individual catalyst beds referred to as a "multi-space bed" system.

Two other references also disclose the utilization of oxygen within a dehydrogenation zone. U.S. Pat. No. 3,502,737 (Ghublikian) presents a process for the dehydrogenation of ethylbenzene which indicates catalyst activity and stability are maintained by the careful control of the amount of oxygen which is present and by reduction in the steam which is used in the reaction zone. An oxygen-containing gas such as air is supplied both initially and at interstage points in a carefully controlled manner. U.S. Pat. No. 3,855,330 (Mendelsohn et al) also discloses a dehydrogenation process using sequential beds of dehydrogenation catalyst and oxidation catalyst. According to the teachings of the '330 reference, it is preferred that oxygen is introduced only after substantial conversion of the feed hydrocarbon, that it is desirable that oxygen does not come into contact with the dehydrogenation catalyst, and that the major part or all of the added oxygen is consumed within the bed of oxidation catalyst.

The use of multi-stage reaction systems in which the catalyst moves downward by gravity flow between different reaction stages is disclosed in U.S. Pat. Nos. 3,761,390 and 3,907,511. These systems are basically directed to the reforming of petroleum naphthas, but may be adapted to the processing of other hydrocarbons.

In U.S. Pat. No. 4,418,237 (Imai), a process is disclosed for the dehydrogenation of a dehydrogenatable hydrocarbon which comprises contacting the dehydrogenatable hydrocarbon with a dehydrogenation catalyst at dehydrogenation conditions in the presence of steam, contacting the resulting mixture of undehydrogenated dehydrogenatable hydrocarbon, resultant dehydrogenated hydrocarbon, hydrogen and steam an oxygen-containing gas in the presence of an oxidation catlyst at oxidation conditions to selectively oxidize hydrogen and recovering said dehydrogenated hydrocarbon.

U.S. Pat. No. 4,435,607 (Imai), a process is disclosed for the dehydrogenation of a dehydrogenatable hydrocarbon with separate and intermediate selective oxidation of hydrogen to thereby raise the temperature of the unconverted and dehydrogenated hydrocarbons before introduction into a subsequent dehydrogenation zone containing dehydrogenation catalyst.

It is believed that there has heretofore been no attempt or description of oxidizing at least a portion of the resulting hydrogen contained in a dehydrogenation zone effluent stream by contacting the effluent stream in admixture with an oxygen-containing stream with a hydrogen selective oxidation catalyst and providing an oxidation zone effluent stream having a reduced concentration of hydrogen and recovering the product hydrocarbon from the oxidation zone effluent stream without contacting the oxidation zone effluent stream with dehydrogenation catalyst. The cited references appear silent in this respect.

BRIEF SUMMARY OF THE INVENTION

The subject invention provides a means of minimizing the heat input and the volume of gas to be compressed by the net gas compressor and which invention employs selective hydrogen combustion of the dehydrogenation zone effluent stream. The invention increases the amount of heat which is available to be exchanged to heat the fresh feed hydrocarbon stream and reduces the volume of gas which must be compressed thereby lowering the cost of utilities and improving the overall economy of the process of the present invention.

One broad embodiment of the invention may be characterized as a process for the catalytic dehydrogenation of a dehydrogenatable $C_2$-plus feed hydrocarbon which comprises the steps of: (a) passing a feed stream comprising the $C_2$-plus feed hydrocarbon into a dehydrogenation zone and through at least one bed of dehydrogenation catalyst maintained at dehydrogenation conditions and producing a dehydrogenation zone effluent stream comprising hydrogen, the $C_2$-plus feed hydrocarbon and a $C_2$-plus product hydrocarbon; (b) forming an oxidation catalyst bed feed stream by admixing an oxygen-containing stream with the dehydrogenation zone effluent stream; (c) passing the oxidation catalyst bed feed stream through a bed of hydrogen selective oxidation catalyst maintained at selective oxidation conditions and producing an oxidation zone effluent stream having a reduced concentration of hydrogen; and (d) recovering the product hydrocarbon from the oxidation zone effluent stream without contacting the oxidation zone effluent stream with dehydrogenation catalyst.

Another embodiment of the invention may be characterized as a process for the catalytic dehydrogenation of a dehydrogenatable $C_2$-plus feed hydrocarbon which comprises the steps of: (a) passing a feed stream comprising the $C_2$-plus feed hydrocarbon into a dehydrogenation zone and through at least one bed of dehydrogenation catalyst maintained at dehydrogenation conditions and producing a dehydrogenation zone effluent stream comprising hydrogen, the $C_2$-plus feed hydrocarbon and a $C_2$-plus product hydrocarbon; (b) forming an oxidation catalyst bed feed stream by admixing an oxygen-containing stream with the dehydrogenation zone effluent stream; (c) passing the oxidation catalyst bed feed stream through a bed of hydrogen selective oxidation catalyst maintained at selective oxidation conditions and producing an oxidation zone effluent stream having a reduced concentration of hydrogen; (d) heat exchanging the oxidation zone effluent stream with the feed stream in step (a) to raise the temperature of the feed stream and to lower the temperature of the oxidation zone effluent stream; and (e) recovering the product hydrocarbon from the oxidation zone effluent stream from step (d) without contacting the oxidation zone effluent stream with dehydrogenation catalyst.

Other embodiments of the subject invention encompass further details such as particular hydrocarbonaceous charge stocks, dehydrogenation catalysts, selective hydrogen oxidation catalysts and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The dehydrogenation of low molecular weight hydrocarbons to produce the corresponding unsaturated hydrocarbons is practiced commercially to provide feedstocks for the petroleum and petrochemical industries. It is expected that there will be increased utilization of these processes in the near future to supply the olefins required for the production of increased amounts of lead-free high octane motor fuels, and as feedstocks for various petrochemical operations.

Processes for the dehydrogenation of aromatic hydrocarbons are also in widespread commercial use. For instance, large quantities of styrene are produced by the dehydrogenation of ethylbenzene. The resultant styrene may be polymerized with itself or it may be copolymerized with butadiene, isoprene, acrylonitrile, etc. Other hydrocarbons which may be dehydrogenated in much the same manner include diethylbenzene, ethyl toluene, propyl benzene, and isopropyl benzene.

The present process can also be applied to the dehydrogenation of other types of hydrocarbons including relatively pure or mixed streams of $C_2$–$C_{16}$ paraffins. The process can therefore be applied to the dehydrogenation of propane, butanes, hexanes or nonanes. However, since the great majority of the present commercial dehydrogenation processes are employed for the dehydrogenation of ethylbenzene, the following description of the subject invention will be presented primarily in terms of the dehydrogenation of ethylbenzene. This is not intended to exclude from the scope of the subject invention those alkylaromatic and acyclic hydrocarbons set out above or those having different ring structures including bicyclic compounds.

Regardless of the type of feedstock charged to a dehydrogenation process and the type or design of the actual catalytic dehydrogenation zone, the resulting effluent from the catalytic dehydrogenation zone comprises hydrogen, unconverted feed hydrocarbon and dehydrogenated hydrocarbon product. This resulting effluent must then be subjected to cooling and fractionation to provide for product separation and purification. During the product separation, the net gas, including primarily the produced hydrogen, must necessarily be compressed for removal from the dehydrogenation process and for subsequent use. In accordance with the present invention, the resulting effluent from the catalytic dehydrogenation zone is admixed with an oxygen-containing stream and then introduced into a selective oxidation zone containing oxidation catalyst whereby at least a portion of the hydrogen is selectively oxidized thereby reducing the volume of net gas which must be compressed and providing additional heat which may then be recovered and utilized in the process. The present invention thereby provides an improved dehydrogenation process having lower overall utility consumption and therefore more economical operation.

As described hereinabove, an oxygen-containing gas stream is admixed with the effluent of the dehydrogenation zone and the resulting admixture is passed into a bed of selective hydrogen oxidation catalyst contained in a selective oxidation zone. To achieve the optimum level of performance and safety in the present process, it is necessary to closely control the rate at which oxygen is passed into the process in this manner. An insufficient amount of oxygen will result in a less than desired consumption of hydrogen and a less than desired reheating of the flowing stream. It is not normally desired to inject an excess amount of oxygen above that required to perform the desired degree of hydrogen combustion. The passage of an excess amount of oxygen into the selective oxidation zone will have detrimental effects upon the long term operation of the process. Operation of the selective oxidation zone in a manner which does not result in the total consumption of the oxygen is undesirable because of the obvious explosive nature of oxygen-hydrocarbon mixtures. The explosive nature of these mixtures can, however, be essentially negated by properly operating the process to avoid the presence of mixtures being within the explosive range, as through the use of diluents and intentionally low oxygen addition rates, and the presence of a sufficient amount of solid material to act as an explosion suppression means. Lastly, the presence of oxygen is not normally desired in vessels containing hydrocarbons as the oxygen may react with the hydrocarbons to form various undesired oxygenated hydrocarbonaceous compounds.

In the drawing, one embodiment of the present invention is illustrated by means of a simplified flow diagram in which such details as pumps, instrumentation, heat exchange and heat-recovery circuits, compressors and similar hardware have been deleted as being non-essential to the understanding of the techniques involved. The use of such miscellaneous appurtenances and recycle streams are well within the purview of one skilled in the art of petroleum refining techniques. With reference now to the drawing, a feed stream comprising relatively high purity ethylbenzene carried by conduit 1 is introduced into the process and heated in feed/effluent heat exchanger 8 and is subsequently admixed with superheated steam from conduit 2 and passed into the dehydrogenation zone 3 via conduit 1. At least a portion of the feed admixture is dehydrogenated to produce styrene and hydrogen. Dehydrogenation zone 3 may be comprised of a multiplicity of dehydrogenation stages. Regardless of the details associated with dehydrogenation zone 3, the effluent from dehydrogenation zone 3 is transported via conduit 4 and is admixed with a high-purity oxygen stream which is introduced via conduit 5. This resulting mixture is introduced via conduit 4 into selective oxidation zone 6 which contains a catalyst which promotes the selective combustion or oxidation of the hydrogen released in the dehydrogenation zone to thereby consume the hydrogen and release heat. By controlling the amount of oxygen which is added through conduit 5, the extent to which the total amount of available hydrogen is combusted within selective oxidation zone 6 may also be controlled. This control is preferably performed on the basis of a temperature measurement taken at the outlet of the selective oxidation zone 6. The rate of oxygen addition through conduit 5 is therefore preferably controlled on the basis of the preferred inlet temperature to feed/effluent heat exchanger 8. The effluent from selective oxidation zone 6 is removed via conduit 7 and introduced into feed/effluent heat exchanger 8 wherein the feed ethylbenzene stream is heated as described hereinabove. The cooled stream from feed/effluent heat exchanger 8 is transported via conduit 7 and is introduced into fractionation zone 13. A low pressure net gas stream comprising normally gaseous hydrocarbons and unoxidized hydrogen, if any, is removed from fractionation zone 13 via conduit 9, compressed in net gas compressor 10 and recovered via conduit 9. A normally liquid hydrocarbonaceous stream comprising unconverted feed hydrocarbon, ethylbenzene, and dehydrogenated feed hydrocarbon, styrene, is removed from fractionation zone 13 via conduit 11 and is introduced into a conventional styrene recovery facility. An aqueous stream comprising condensed feed steam and the water resulting from the selective oxidation of hydrogen is removed from fractionation zone 13 via conduit 12 and recovered.

The subject invention has the advantage of reducing the quantity of noncondensible gas which must be compressed and removed from the process. A second advantage is the reduction of utility consumption which is realized by the lower quantity of utilities required to compress the net gas and the ability to recover the heat regenerated by the selective oxidation of hydrogen in order to preheat the incoming hydrocarbon feedstock.

The subject process may be employed with a wide range of feedstocks. The feed hydrocarbon may therefore include $C_6$-plus cyclic and acyclic hydrocarbons including $C_6$ paraffins, $C_7$ paraffins, ethylbenzene and other alkylaromatic hydrocarbons. Other suitable feedstocks comprise a light hydrocarbon, a term used herein to refer to a hydrocarbon having less than six carbon atoms per molecule including ethane. The utilization of the subject process with any particular hydrocarbon will of course depend on an economic evaluation of the cost of utilizing the subject process compared with the benefits with which it provides.

The conditions which will be employed in the dehydrogenation zone of the process will vary depending on such factors as feedstock, catalyst activity, and desired conversion. A general range of conditions which may be employed for dehydrogenation include a temperature from about 550° C. to about 800° C., a pressure from about 0.3 to about 20 atmospheres absolute and a liquid hourly space velocity from about 0.5 to about 20 $hr^{-1}$. For the dehydrogenation of propane, for example, the preferred conditions include a temperature in the range of about 600° C. to about 700° C., a pressure from about 1 to about 3 atmospheres, a liquid hourly space velocity of about 1 to about 10 $hr^{-1}$ and a hydrogen to total hydrocarbon ratio between 1:1 and 5:1. It is especially preferred that the inlet temperature to each bed of propane dehydrogenation catalyst is between 650° C. and 690° C. The pressure in the reaction zone employed within the process preferably differs only by the incidental pressure drop which occurs as the reactants pass through the overall reaction system. The pressure maintained in the selective oxidation zone is therefore essentially the same as the pressure in the dehydrogenation zone. The inlet temperature of the bed of selective oxidation catalyst is preferably between 10° and 20° C. below the desired inlet temperature of the dehydrogenation catalyst in the dehydrogenation zone. Larger temperature increases in the oxidation zone may be possible and desired depending on the selectivity of the oxidation catalyst and the degree of hydrogen conversion desired.

The dehydrogenation zone may utilize any convenient system for the catalytic dehydrogenation of the hydrocarbon feedstock. The dehydrogenation zone preferably comprises at least one radial flow reactor in which the catalyst gradually moves downward by gravity flow to allow the near continuous replacement of used catalyst with catalyst having a higher activity. Preferably, this replacement catalyst is regenerated in the appropriate facilities after being removed from the lowermost portion of the unitary multi-stage dehydrogenation reaction zone. It is preferred that a multi-stage reaction zone in which the reactants make at least two, preferably three, passes through a catalyst bed is employed. The dehydrogenation catalyst therefore preferably enters the top of a single unitary outer vessel containing the separate dehydrogenation stages and flows downward through the vessel from stage to stage by the action of gravity. A detailed description of moving bed reactors may be obtained by reference to U.S. Pat. Nos. 3,647,680; 3,652,231; 3,706,536; 3,785,963; 3,825,116; 3,839,196; 3,839,197; 3,854,887; and 3,856,662.

A preferred propane dehydrogenation catalyst comprises a platinum group component, a tin component and an alkali metal component and a porous inorganic carrier material. Other catalytic compositions may be used within the dehydrogenation zone if desired.

It is preferred that the porous carrier material of the hereinabove described dehydrogenation catalyst is an absorptive high surface area support having a surface area of about 25 to about 500 $m^2/g$. The porous carrier material should be relatively refractory to the conditions utilized in the reaction zone and may be chosen from those carrier materials which have traditionally been utilized in dualfunction hydrocarbon conversion catalysts. A porous carrier material may therefore be chosen from an activated carbon, coke or charcoal, silica or silica gel, clays and silicates including those synthetically prepared and naturally occurring, which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria; crystalline aluminosilicates such as naturally occurring or synthetically prepared mordenite or a combination of one or more of these materials. A preferred porous carrier material is a refractory inorganic oxide, with the best results being obtained with an alumina carrier material. The crystalline aluminas, such as gamma-alumina, give the best results. In general, the preferred catalyst will have a gamma-alumina carrier which is in the form of spherical particles having a relatively small diameter on the order of about 1/16 inch.

A preferred alumina carrier material for the dehydrogenation catalyst may be prepared in any suitable manner. For example, the alumina carrier may be prepared by adding a suitable alkaline reagent, such as ammonium hydroxide, to a salt of aluminum such as aluminum chloride in an amount to form an aluminum hydroxide gel which upon drying and calcining is converted to alumina. It is particularly preferred that alumina spheres are manufactured by the well-known oil drop method which comprises forming an alumina hydrosol by these techniques taught in the art, and preferably by reacting aluminum metal with hydrochloric acid and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C. to about 200° C. and calcined at a temperature of about 450° C. to about 700° C. for a period of about 1 to about 20 hours. See the teachings of U.S. Pat. Nos. 2,620,314 and 4,250,058 for additional details on the preparation of the base material by the oil drop method.

A preferred dehydrogenation catalyst as described hereinabove also contains a platinum group component. Of the platinum group metals which include palladium, rhodium, ruthenium, osmium, and iridium, the use of platinum is preferred. The platinum group components may exist within the final catalyst composite as a compound such as an oxide, sulfide, halide, oxysulfide, or as an elemental metal or in combination with one or more other ingredients of the catalyst. It is believed that best results are obtained when substantially all the platinum group component exists in the elemental state. The platinum group component generally comprises from about 0.01 to about 2 weight percent of the final catalytic composite, calculated on an elemental basis. It is preferred that the platinum content of the catalyst is between about 0.1 and 1 weight percent. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the hereinabove mentioned dehydrogenation catalyst should constitute about 0.01 to about 5 weight percent of the final composite, calculated on an elemental basis, although substantially higher amounts of tin may be utilized in some cases. Best results are often obtained with about 0.1 to about 1 weight percent tin. It is preferred that the atomic ratio of tin to platinum is between 1:1 and 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

A preferred catalyst as hereinabove described contains an alkali metal component chosen from cesium, rubidium, potassium, sodium and lithium. The preferred alkali metal is normally either potassium or lithium depending on the feed hydrocarbon. The concentration of the alkali metal may range from between 0.1 and 3.5 weight percent but is preferably between 0.2 and about 2.5 weight percent calculated on an elemental basis. This component may be added to the catalyst by the method described above as a separate step or simultaneously with the addition of another component. With some alkali metals, it is normally necessary to limit the halogen content to less than 0.5 weight percent and preferably less than 0.1 weight percent.

Dehydrogenation catalysts generally consist of one or more metallic components selected from Groups VI and VIII of the Periodic Table. One typical catalyst for the dehydrogenation of alkylaromatic hydrocarbons comprises 85 percent by weight ferric oxide, 2 percent chromia, 12 percent potassium hydroxide and 1 percent sodium hydroxide. A second dehydrogenation catalyst, which is used commercially, consists of 87-90 percent ferric oxide, 2-3 percent chromium oxide and 8-10 percent potassium oxide. A third typical catalyst comprises 90 percent by weight iron oxide, 4 percent chromia and 6 percent potassium carbonate. Methods for preparing suitable catalysts are well known to the art. This is demonstrated by the teachings of U.S. Pat. No. 3,387,053, which describes the manufacture of a catalytic composite of at least 35 weight percent iron oxide as an active catalytic agent, from about 1-8 weight percent zinc or copper oxide, about 0.5-50 weight percent of an alkali promoter and from about 1-5 weight percent chromic oxide as a stabilizer and a binding agent. U.S. Pat. No. 4,467,046 also describes a catalyst for the dehydrogenation of ethylbenzene in the presence of steam. This catalyst consists of 15 to 30 weight percent potassium oxide, 2 to 8 percent cerium oxide, 1.5 to 6 percent molybdenum oxide, 1 to 4 percent calcium carbonate, with the balance iron oxide.

The selective oxidation catalyst employed in the subject process may be any commercially suitable catalyst which meets the required standards for stability and activity and which possesses high selectivity for the oxidation of hydrogen as compared to the oxidation of the feed or product hydrocarbon. That is, the oxidation catalyst must have a high selectivity for the oxidation of hydrogen with only small amounts of the feed or product hydrocarbon being oxidized. A preferred oxidation catalyst comprises a Group VIII noble metal, a Group IVA metal and a metal or metal cation which possesses a crystal ionic radius greater than 1.3 A, with these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5 weight percent of the finished catalyst. Of the metals of Group IVA of the Periodic Table, germanium, tin and lead comprise the preferred species, these metals being present in the final catalyst composite in an amount from about 0.01% to about 5% by weight. The metal or metal cation having a radius greater than 1.3 A is preferably chosen from Groups IA or IIA and is present in an amount equal to 0.01 to about 10 weight percent of the finished catalyst. This component of the catalyst may include lithium, sodium, potassium, cesium, rubidium, calcium, francium, strontium and barium. A particularly preferred oxidation catalyst comprises platinum, tin and lithium. Further details of a preferred selective oxidation catalyst are provided in U.S. Pat. No. 4,652,687 (Imai et al).

The preferred solid support for the selective oxidation catalyst is alumina having a surface area between 1 and 300 m$^2$/g and apparent bulk density of between about 0.2 and 1.5 g/cc and an average pore size greater than 20 A. The metal-containing components are preferably impregnated into solid particles of the solid support by immersion in an aqueous solution followed by drying and calcination at a temperature of from about 500° C. to 600° C. in air. The support may be in the form of spheres, pellets or extrudates.

The operating conditions utilized during the contacting of the dehydrogenation zone effluent stream with the oxidation catalyst contained in the selective oxidation zone will be, to a large extent, set by the previously referred to dehydrogenation conditions. The inlet temperature of the selective oxidation zone will be necessarily determined by the temperature of the dehydrogenation zone effluent, and the temperature of the oxygen which is introduced into the selective oxidation catalyst contained in the selective oxidation zone. The increase in temperature in the selective oxidation zone during the passage of the reactant stream will depend upon the available quantity of hydrogen and the amount of oxygen introduced into the selective oxidation zone. The outlet temperature of the selective oxidation zone will be necessarily influenced by the degree of selective oxidation of the hydrogen within the oxidation zone. In accordance with the present invention, a prime objective is to combust or oxidize a significant amount of the hydrogen present in the dehydrogenation zone effluent stream in the selective oxidation zone in order to reduce the quantity of hydrogen which must be subsequently compressed and to generate heat which may be recovered and utilized within the process and particularly to heat the incoming fresh feed stream. The temperature and pressure conditions maintained in the selective oxidation zone preferably include a temperature from about 500° C. to about 800° C. and a pressure from about 0.3 to about 20 atmospheres absolute. The space velocity through the oxidation catalyst may preferably range from about 0.5 to about 20 $hr^{-1}$. The liquid hourly space velocity, based on the liquid hydrocarbon charge at 60° F. (15° C.) is preferably between about 1 and about 20 $hr^{-1}$. It is that substantially all of the oxygen which enters the selective oxidation zone is consumed within that zone and that the effluent stream from the selective oxidation zone contains less than 0.1 mole percent oxygen. The total amount of oxygen charged to the selective oxidation zone may be readily determined by an artisan based upon the degree of hydrogen consumption desired and the outlet temperature of the selective oxidation zone which is required. The oxygen source may be air, but it is preferred that an oxygen-enriched gas containing less than 5 mole percent of nitrogen or other impurities is used as the oxygen source. To avoid any cooling of the selective oxidation zone effluent the oxygen-containing gas stream should preferably be heated to a temperature equal to the temperature of the inlet to the selective oxidation zone. In accordance with the present invention, the selective oxidation catalyst may be employed or installed in the selective oxidation zone in any convenient manner known in the art.

The effluent stream removed from the selective oxidation zone is heat exchanged for the purpose of lowering its temperature for the recovery of heat. This effluent stream may be heat exchanged against a stream of steam, a reactant stream of this or another process or used as a heat source for fractionation. Commercially, this effluent stream is often passed through several heat exchanges thereby heating a number of different streams including the incoming hydrocarbon feedstock. This heat exchange is performed subject to the constraints set out above. The subsequently cooled effluent stream from the selective oxidation zone is passed into a fractionation zone as a mixed phase stream to allow the facile crude separation by decantation of the hydrocarbons from the water and any net gas including any unreacted hydrogen present in the effluent stream. In accordance with one embodiment of the present invention, the styrene present in the fractionation zone becomes part of a hydrocarbon stream which is withdrawn from the fractionation zone and transferred to proper downstream separation facilities. Preferably, the styrene or other product hydrocarbon is recovered from the hydrocarbon stream by using one of the several fractionation systems known in the art. This fractionation will preferably yield a relatively pure stream of ethylbenzene, which is recycled, and an additional stream comprising benzene and toluene. These two aromatic hydrocarbons are by-products of the dehydrogenation reaction. They may be recycled in part as taught in U.S. Pat. No. 3,409,689 and British Pat. No. 1,238,602 or entirely rejected from the process. Styrene is recovered as a third stream which is withdrawn from the process. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon-6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080 and 3,517,081.

The recovery of styrene through the use of fractionation is described in several references including U.S. Pat. No. 3,525,776. In this reference, the hydrocarbonaceous phase removed from the initial fractionation zone is passed into a first column referred to as a benzene-toluene column. This column is operated at a subatmospheric pressure to allow its operation at lower temperatures and hence reduce the rate of styrene polymerization. Various inhibitors such as elemental sulfur for example are injected into the column for this same purpose. Sulfur can also be introduced into this column by returning at least a portion of the high molecular weight material separated from the bottom stream of a styrene purification column. A more detailed description of this is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream preferably contains at least 95 mole percent benzene and toluene. The bottoms of the benzene-toluene column is passed into second fractionation column from which ethylbenzene is removed as an overhead product and recycled. The bottoms stream of this column is then purified to obtain the styrene. Product recovery techniques directed to the recovery of vinyl toluene via fractionation and the use of chemical additives to inhibit polyerization are described in U.S. Pat. Nos. 4,417,085 and 4,492,675. The use of inhibitors and alternative fractionation techniques for readily polymerizable vinyl aromatic compounds is also described in U.S. Pat. No. 4,469,558.

As previously mentioned, the subject process is not limited to the production of styrene and may be used to produce para methyl styrene by dehydrogenation of ethyl toluene or for the production of other unsaturated product hydrocarbons such as acyclic $C_3$–$C_8$ olefins. The product hydrocarbon recovered from the process may therefore be propylene, a butylene or a mixture of butylenes, a heptene, etc.

The foregoing description and drawing clearly illustrate the advantages encompassed by the process of the present invention and the benefits to be afforded with the use thereof.

We claim as our invention:

1. A process for the catalytic dehydrogenation of a dehydrogenatable $C_2$-plus feed hydrocarbon which comprises the steps of:

(a) passing a feed stream comprising said $C_2$-plus feed hydrocarbon into a dehydrogenation zone and through at least one bed of dehydrogenation catalyst maintained at dehydrogenation conditions and producing a dehydrogenation zone effluent stream comprising hydrogen, the $C_2$-plus feed hydrocarbon and a $C_2$-plus product hydrocarbon;

(b) forming an oxidation catalyst bed feed stream by admixing an oxygen-containing stream with said dehydrogenation zone effluent stream;

(c) passing the oxidation catalyst bed feed stream through a bed of hydrogen selective oxidation catalyst maintained at selective oxidation conditions and producing an oxidation zone effluent stream having a reduced concentration of hydrogen; and (d) recovering the product hydrocarbon from said oxidation zone effluent stream without contacting said oxidation zone effluent stream with dehydrogenation catalyst.

2. The process of claim 1 wherein said feed hydrocarbon comprises alkylaromatic hydrocarbons.

3. The process of claim 2 wherein said alkylaromatic hydrocarbons are the group consisting of ethylbenzene, diethylbenzene, ethyl toluene, propyl benzene and isopropyl benzene.

4. The process of claim 1 wherein said feed hydrocarbon comprises $C_2-C_{16}$ paraffins.

5. The process of claim 4 wherein said $C_2-C_{16}$ paraffins are selected from the group consisting of propane, butane, hexane and nonane.

6. The process of claim 1 wherein said dehydrogenation catalyst comprises a platinum group component, a tin component, an alkali metal component and a porous inorganic carrier material.

7. The process of claim 1 wherein said dehydrogenation catalyst comprises ferric oxide and chromia.

8. The process of claim 1 wherein said dehydrogenation conditions include a temperature from about 550° C. to about 800° C., a pressure from about 0.3 to about 20 atmospheres absolute and a liquid hourly space velocity from about 0.5 to about 20 $hr^{-1}$.

9. The process of claim 1 wherein said hydrogen selective oxidation catalyst comprises a Group VIII noble metal and a metal or metal cation which possesses a crystal ionic radius greater than 1.3 A.

10. The process of claim 1 wherein said hydrogen selective oxidation catalyst comprises platinum, lithium and alumina.

11. The process of claim 1 wherein said selective oxidation conditions include a temperature from about 500° C. to about 800° C., a pressure from about 0.3 to about 20 atmospheres absolute and a liquid hourly space velocity from about 1 to about 20 $hr^{-1}$.

12. The process of claim 1 wherein said oxygen-containing stream contains less than 5 mole percent of nitrogen.

13. A process for the catalytic dehydrogenation of a dehydrogenatable $C_2$-plus feed hydrocarbon which comprises the steps of:

(a) passing a feed stream comprising said $C_2$-plus feed hydrocarbon into a dehydrogenation zone and through at least one bed of dehydrogenation catalyst maintained at dehydrogenation conditions and producing a dehydrogenation zone effluent stream comprising hydrogen, the $C_2$-plus feed hydrocarbon and a $C_2$-plus product hydrocarbon;

(b) forming an oxidation catalyst bed feed stream by admixing an oxygen-containing stream with said dehydrogenation zone effluent stream;

(c) passing the oxidation catalyst bed feed stream through a bed of hydrogen selective oxidation catalyst maintained at selective oxidation conditions and producing an oxidation zone effluent stream having a reduced concentration of hydrogen;

(d) heat exchanging said oxidation zone effluent stream with said feed stream in step (a) to raise the temperature of said feed stream and to lower the temperature of said oxidation zone effluent stream; and (e) recovering the product hydrocarbon from said oxidation zone effluent stream from step (d) without contacting the oxidation zone effluent stream with dehydrogenation catalyst.

14. The process of claim 13 wherein said feed hydrocarbon comprises alkylaromatic hydrocarbons.

15. The process of claim 14 wherein said alkylaromatic hydrocarbons are selected from the group consisting of ethylbenzene, diethylbenzene, ethyl toluene, propyl benzene and isopropyl benzene.

16. The process of claim 13 wherein said feed hydrocarbon comprises $C_2-C_{16}$ paraffins.

17. The process of claim 15 wherein said $C_2-C_{16}$ paraffins are selected from the group consisting of propane, butane, hexane and nonane.

18. The process of claim 13 wherein said dehydrogenation catalyst comprises a platinum group component, a tin component, an alkali metal component and a porous inorganic carrier material.

19. The process of claim 13 wherein said dehydrogenation catalyst comprises ferric oxide and chromia.

20. The process of claim 13 wherein said dehydrogenation conditions include a temperature from about 550° C. to about 800° C., a pressure from about 0.3 to about 20 atmospheres absolute and a liquid hourly space velocity from about 0.5 to about 20 $hr^{-1}$.

21. The process of claim 13 wherein said hydrogen selective oxidation catalyst comprises a Group VIII noble metal and a metal or metal cation which possesses a crystal ionic radius greater than 1.3 A.

22. The process of claim 13 wherein said hydrogen selective oxidation catalyst comprises platinum, lithium and alumina.

23. The process of claim 13 wherein said selective oxidation conditions include a temperature from about 500° C. to about 800° C., a pressure from about 0.3 to about 20 atmospheres absolute and a liquid hourly space velocity from about 1 to about 20 $hr^{-1}$.

24. The process of claim 13 wherein said oxygen-containing stream contains less than 5 mole percent of nitrogen.

* * * * *